United States Patent [19]

Landgraf et al.

[11] Patent Number: 4,647,081
[45] Date of Patent: Mar. 3, 1987

[54] BALL CATCH COUPLING FOR RELEASABLY CONNECTING TWO PARTS PERMITTING RELATIVE ROTATION OF THE PARTS WHEN CONNECTED

[75] Inventors: Hermann Landgraf; Werner Schuss; Werner Schwarz, all of Heppenheim, Fed. Rep. of Germany

[73] Assignee: Siemens Aktiengesellschaft, Berlin and Munich, Fed. Rep. of Germany

[21] Appl. No.: 785,536

[22] Filed: Oct. 8, 1985

[30] Foreign Application Priority Data

Nov. 5, 1984 [DE] Fed. Rep. of Germany ....... 3440341

[51] Int. Cl.$^4$ .............................................. F16L 37/08
[52] U.S. Cl. .................................... 285/304; 285/317; 285/276; 433/126
[58] Field of Search ................... 285/276, 277, 1, 304, 285/317; 433/132, 131, 126

[56] References Cited

U.S. PATENT DOCUMENTS

| 1,953,830 | 4/1934 | Park | 285/322 X |
| 2,111,956 | 3/1938 | Baldwin | 285/277 X |
| 2,434,684 | 1/1948 | Casperson | 285/276 |
| 2,448,688 | 9/1948 | Scheiwer | 285/304 X |
| 2,452,430 | 10/1948 | Clark et al. | 285/304 X |
| 3,144,237 | 8/1964 | Zurit et al. | |
| 3,317,220 | 5/1967 | Bruning | 285/304 X |
| 4,431,412 | 2/1984 | Lares et al. | |

FOREIGN PATENT DOCUMENTS

| 583718 | 8/1933 | Fed. Rep. of Germany . | |
| 2004610 | 4/1979 | United Kingdom | 285/304 |

Primary Examiner—Dave W. Arola
Attorney, Agent, or Firm—Hill, Van Santen, Steadman & Simpson

[57] ABSTRACT

A ball catch coupling for releasably connecting two parts which permits relative rotation of the parts in the connected conditions as an annular section carried on one of the parts with a number of uniformly disposed bores at a periphery thereof, balls respectively received and rotatable in each of the bores, a closed resilient ring surrounding the balls, an annular groove in the annular section which receives the ring and permits limited axial displacement and free rotation thereof within said groove, and the other part to be connected having an annular groove which at least partially receives the ring and the balls when the two parts are connected. The limited displacement and free rotation of the ring with respect to the annular section permits engagement and disengagement to be undertaken particularly easily and with low wear.

7 Claims, 4 Drawing Figures

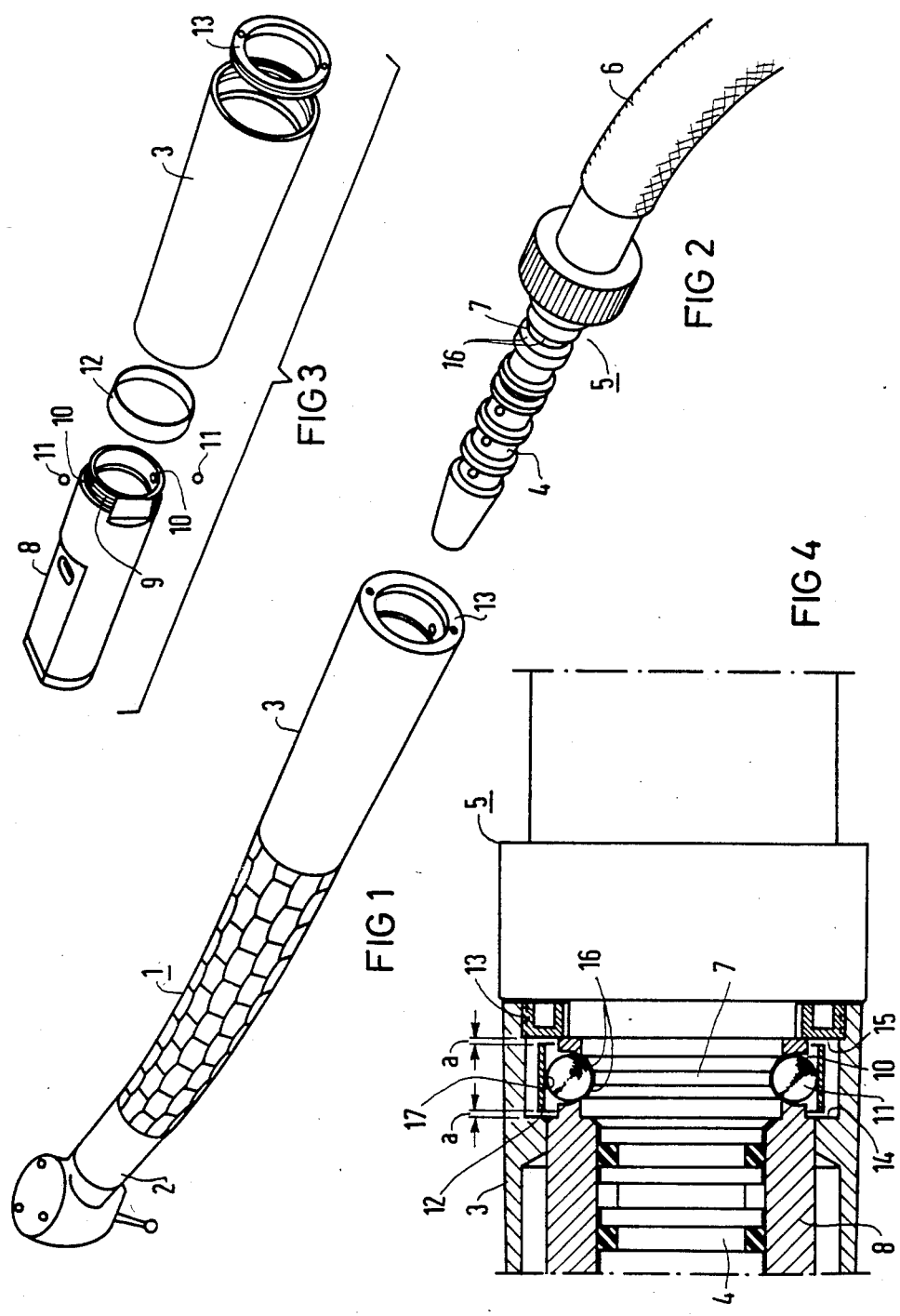

4,647,081

BALL CATCH COUPLING FOR RELEASABLY CONNECTING TWO PARTS PERMITTING RELATIVE ROTATION OF THE PARTS WHEN CONNECTED

BACKGROUND OF THE INVENTION

1. Field of the Invention

The present invention relates to ball catch couplings for rapid axial connection and release of two parts, such as two components of a dental handpiece, and which permits relative rotation of the parts with respect to each other in the connected condition. In particular the invention relates to a coupling having balls disposed at the circumference of one of the parts in a transverse plane contained in bores of a cylindrical section, the balls engaging an annular groove carried in the other part in the coupled condition.

2. Description of the Prior Art

A coupling device for dental tools is described in German patent No. 583,718 wherein the tool is driven by a flexible shaft and has a ball catch device having at least one catch ball which engages a catch groove in a separable part by means of a resilient open ring. The resilient ring has a plurality of catch bores at a circumference thereof which function to adjust the pressure acting on the ball. Automatic decoupling given overload of the two flexible shafts to be connected is achieved with this ball catch device. The catch device, therefore, does not function to permit fast axial coupling and decoupling of the parts, and further does not permit free rotation of the parts with respect to each other when connected.

Another ball catch device is described in U.S. Patent No. 4,431,412 wherein three spring-loaded balls are provided at the circumference of one portion of a handpiece, these balls engaging an annular groove at the circumference of the other handpiece part. The balls and the springs are held in place by a closed, non-resilient ring.

A disadvantage of such conventional ball catch devices is that the balls are pressed so tightly against the catch surfaces in which they are received during a catching operation as well as during an unlocking operation, such that the balls are no longer freely rotatable and are therefore drawn or scraped across the catch faces. Due to the lack of free rotation of the balls in this condition, the balls and the catch faces corresponding therewith are heavily worn given frequent coupling and decoupling.

SUMMARY OF THE INVENTION

It is an object of the present invention to provide a ball catch device for rapid coupling and decoupling of two parts which permits relative rotation of the parts when coupled and which reduces wear of the balls and catch surfaces to a minimum.

The above object is inventively achieved in a ball catch device having a plurality of balls carried in bores at the circumference of one of the parts to be connected, the balls being freely rotatable in the bores and being covered by a continuous resilient ring. The ring is freely rotatable in the part in which the balls are mounted and is also slightly axially displaceable with respect thereto within limits. The balls and the ring are at least partially received in a mating annular groove and the other part to be connected therewith. The resilient ring permits the balls to roll without undue friction even in the presence of extremely high forcing action both during rotation of the two parts when coupled, and during the catching and unlocking operations, i.e., given axial movement. Where is thereby reduced to a minimum. If the engagement depth of the balls within annular grooves is selected such that the balls roll only against the lateral surfaces of the annular groove such that the floor or base of the groove is not in contact with the balls, the axial play between the parts to be connected can be reduced to a minimum in the coupled condition.

DESCRIPTION OF THE DRAWINGS

FIG. 1 is a perspective view of a first part to be connected, such as a portion of a dental handpiece.

FIG. 2 is a perspective view of a portion of a second part to be connected to the part shown in FIG. 1, such as a hose leading to a dental handpiece.

FIG. 3 is an exploded view of a ball catch coupling constructed in accordance with the principles of the present invention.

FIG. 4 is a side sectional view showing the parts of FIG. 1 and FIG. 2 in a coupled condition in accordance with the principles of the present invention.

DESCRIPTION OF THE PREFERRED EMBODIMENTS

A perspective illustration of a first part to be coupled to another part is shown in FIG. 1. In the embodiment described herein the part shown in FIG. 1 (and the complementary part shown in FIG. 2) are portions of a dental turbine handpiece, generally referenced at 1, which has a distal portion 2 for accepting a rotating tool (not shown), and which has a hollow sleeve at its opposite end.

The complementary mating part is generally referenced at 5 in FIG. 2, and has a connecting tube 4 in fluid communication with a supply hose 6. The tube 4 can be axially introduced into the sleeve 3 of the handpiece 1. The tube 4, when connected within the sleeve 3, is freely rotatable in the coupled condition. A ball catch coupling is provided for this purpose, shown in detail in FIGS. 3 and 4. The details of the tube 4 are of a conventional design, and need not be described in greater detail, other than an annular groove 7 which is provided in the tube 4, the annular groove 7 being an operative portion of the ball catch coupling described below.

The sleeve 3 of the handpiece 1 has an insert 8, flattened at the top, which is also in the form of a sleeve and which has an end facing the connection tube 5 which is provided with a recess 9. The recess 9 has at least two bores 10 therein disposed in a transverse plane and uniformly distributed around the circumference or periphery of the recess 9. Each of the bores 10 receives a ball 11 with the ball 11 being freely rotatable within the bore 10. The balls 11 are received in the bores 10 so as to project slightly therefrom toward the inside of the handpiece 1, however slight flanges are provided so as to prevent the balls 11 from falling out of the bores 10. A closed resilient ring 12 is further provided as part of the ball catch coupling disclosed herein which surrounds the balls 11 and presses resiliently thereagainst. The ring 12 is disposed within the connected parts so as to have limited axial movement with respect thereto. The end face of the handpiece 1 is closed with a screw ring 13.

The two parts 1 and 5 are shown in connected condition in FIG. 4 in longitudinal section in the region of the coupling device. The resilient ring 12, which exerts a pressing force on the balls 11 necessary for engagement, is in the form of an elongated cylinder and is supported in the sleeve 3 of the handpiece 1 with limited axial play designated at a on both sides thereof. One limiting detent is formed by a collar 14 of the insert 8, the other limiting detent is formed by an end face surface 15 of the screw ring 13.

The bores 10 are of dimensions selected such that the balls 11 project inwardly to such a degree that adequate engagement with the annular groove 7 in the connecting tube 4 is insured. The annular groove 7 in the tube 4 has slanted surfaces 16 disposed such that the balls 11 can roll on the surfaces in the connected condition in a three-point seating formed by the two lateral surfaces and the seating surface 17 of the ball 11 on the ring 12. The base of the groove 7 is thus not in contact with the balls 11, thereby reducing friction into a minimum.

When coupling and decoupling the parts 1 and 5, the balls 11 in the bores 10 are first pressed radially outwardly, causing the resilient ring 12 to be deformed to an oval. The balls 11 are thereby disengaged from the annular groove 7 by rolling against the groove surfaces 16, and are moved radially outwardly in the bores 10. Because the ring 12 is freely rotatable and presses against the balls 11 with limited axial play a at both sides, the balls 11 can roll both in the axial direction and in the direction of the circumference of the ring without limitation. Depending upon whether coupling or decoupling is being undertaken, the ring 12 can displace itself within the limits a toward the left or toward the right up to one of the detents 14 or 15. Axial motion transmitted onto the balls 11 during coupling and decoupling operations thus simply causes the balls 11 to roll on the walls 16, i.e., rotation of the balls 11 is not inhibited. Where on the parts is thereby reduced and their useful life is increased.

The ball catch device disclosed herein may be used for connection any two parts for which relative rotation after connection is desired, however, is particularly suited for connecting a turbine handpiece to the connection armature of a supply hose in a dental device.

Although other modifications and changes may be suggested by those skilled in the art it is the intention of the inventors to embody within the patent warranted hereon all changes and modifications as reasonably and properly come within the scope of their contribution to the art.

We claim as our invention:

1. A ball catch coupling for releasably connecting two parts permitting relative rotation of said parts when connected comprising:
    an annular section of one of said parts having a plurality of uniformly disposed bores at a periphery thereof;
    a like plurality of balls respectively received and rotated in said bores;
    a circumferentially continuous resilient ring surrounding said balls;
    means for mounting said resilient ring on said one of said parts permitting limited axial displacement and free rotation of said ring with respect to said one of said parts; and
    the other of said parts having an annular groove at least partially receiving said balls when said parts are connected.

2. A ball catch coupling as claimed in claim 1 wherein said resilient ring is an axially extended cylinder.

3. A ball catch device as claimed in claim 1 wherein said annular section is a cylindrical sleeve received in said one of said parts, and further comprising a screw ring for axially retaining said sleeve in said one of said parts, and wherein said means for mounting said resilient ring is an annular groove in said sleeve having one wall for limiting axial displacement of said ring in one axial direction, and abutting said screw ring for limiting axial displacement of said ring in an opposite axial direction.

4. A ball catch coupling as claimed in claim 1 wherein said annular groove in said other part has spaced lateral surfaces disposed for contacting said balls when said parts are connected and preventing contact of said balls within the other surface of said groove.

5. A ball catch coupling as claimed in claim 4 wherein said surfaces of said annular groove are V-shaped in cross-section.

6. A ball catch coupling as claimed in claim 1 wherein said one of said parts is a dental turbine handpiece, and wherein the other of said parts is a supply hose for said turbine.

7. A ball catch coupling for axially releasably connecting a first part having an axial cylindrical recess therein with a second part having a tube axially insertable in said cylindrical recess of said first part, said coupling permitting relative rotation of said first and second parts when connected and comprising:
    a cylindrical sleeve axially received in said recess in said first part surrounding said tube of said second part, said sleeve having an annular recess at one end thereof with a plurality of uniformly disposed bores therein, said annular recess having one transverse wall;
    a plurality of balls respectively received and freely rotatable in said bores;
    a closed resilient ring surrounding said balls and received in said groove;
    a screw retainer ring threadedly received at said end of said sleeve having an inner transverse wall, said transverse wall of said annular groove and said inner transverse wall of said screw ring being spaced when assembled or permitting limited axial displacement and free rotation of said resilient ring with respect to said first part; and
    said second part having an annular groove therein disposed when said first and second parts are connected for said partially receiving said balls.

* * * * *